US011771591B2

(12) United States Patent
Agarwal et al.

(10) Patent No.: US 11,771,591 B2
(45) Date of Patent: Oct. 3, 2023

(54) LIQUID MEDICATION DISPENSING APPARATUS

(71) Applicant: LUMIO HEALTH INC., San Jose, CA (US)

(72) Inventors: Aakash Kumar Agarwal, San Jose, CA (US); Mark Yeghiazarian, El Cajon, CA (US); Kumar Nadhan, Foster City, CA (US)

(73) Assignee: Lumio Health Inc., San Jose, CA (US)

( * ) Notice: Subject to any disclaimer, the term of this patent is extended or adjusted under 35 U.S.C. 154(b) by 159 days.

(21) Appl. No.: 17/403,822

(22) Filed: Aug. 16, 2021

(65) Prior Publication Data

US 2022/0047418 A1 Feb. 17, 2022

Related U.S. Application Data

(60) Provisional application No. 63/066,666, filed on Aug. 17, 2020.

(51) Int. Cl.
*A61F 9/00* (2006.01)

(52) U.S. Cl.
CPC .................... *A61F 9/0008* (2013.01)

(58) Field of Classification Search
CPC ............. A61F 9/0008; A61F 9/0026; A61M 2210/0612; A61M 11/00; A61M 35/003; A61M 11/007; A61M 11/02; A61M 5/31511; A61M 5/315; A61M 5/31515; A61M 11/006; A61M 11/008; A61M 2005/2403; A61M 2005/2407; A61M 2005/2411; A61M 2005/2414; A61M 5/142; A61M 2005/14208;

(Continued)

(56) References Cited

U.S. PATENT DOCUMENTS

| 4,154,375 | A | * | 5/1979 | Bippus | ................. | H01H 3/0206 |
| | | | | | | 200/61.86 |
| 5,346,132 | A | | 9/1994 | Hahn et al. | | |
| 6,033,384 | A | | 3/2000 | Py | | |
| 6,302,101 | B1 | * | 10/2001 | Py | ....................... | B05B 11/1066 |
| | | | | | | 128/200.22 |

(Continued)

FOREIGN PATENT DOCUMENTS

WO 2018088607 5/2018

*Primary Examiner* — Nicholas J. Weiss
*Assistant Examiner* — Brandon W. Levy
(74) *Attorney, Agent, or Firm* — Kanika Radhakrishnan; Evergreen Valley Law Group

(57) ABSTRACT

Various embodiments of the present disclosure provide a liquid medication dispensing apparatus. The apparatus includes a housing including an inner cavity and a cap operable between an open position and a closed position. A cartridge assembly is configured to be inserted in the inner cavity. The cartridge assembly includes a support structure, a mounting platform, a nozzle base including a nozzle, and an intermediate body portion coupling the support structure and the nozzle base while maintaining a gap therebetween. The apparatus includes a control unit disposed in the housing. The control unit is configured to receive a first signal from a circuitry associated with a dispensing button, upon detection of an input on the dispensing button. Upon receipt of the first signal, the control unit provides a command signal to a drive mechanism for retrieving a liquid medication from a medication bottle and extrude the liquid medication through the nozzle.

19 Claims, 14 Drawing Sheets

(58) Field of Classification Search
CPC ...... A61M 5/14212; A61M 2205/8206; A61M 11/042; A61M 15/08; A61M 11/001; A61M 15/0081; A61M 15/0065; A61M 2205/3584; A61M 2205/3306; A61M 15/0026; A61M 15/0025; A61K 9/0048; A61K 9/12; A61P 27/02; B05B 17/0676; B05B 17/0607; B05B 11/1052; B05B 11/02; B05B 9/0413; B05B 9/0855; B05B 9/0861; B05B 11/10; B05B 11/1001; B05B 9/0866; B05B 11/0038; B05B 11/1011; B05B 11/0097; B05B 11/1004; B05B 11/1057; G16H 20/13; G16H 20/17; B65D 47/18; B65D 1/08; B65D 25/42; A61H 35/02; A61H 2205/024; A45D 2200/057; A24F 40/00; A24F 40/10; A24F 40/42

See application file for complete search history.

(56) References Cited

U.S. PATENT DOCUMENTS

| | | | |
|---|---|---|---|
| 8,998,861 | B2 | 4/2015 | Fateh |
| 9,549,847 | B2 | 1/2017 | Marx |
| 10,314,740 | B2 | 6/2019 | Kraft |
| 2008/0149098 | A1 | 6/2008 | Bonney et al. |
| 2016/0051776 | A1* | 2/2016 | Von Hollen ........ A61M 15/009 128/203.14 |
| 2016/0193434 | A1* | 7/2016 | Gleixner ............... A61M 11/06 128/200.14 |
| 2017/0028132 | A1* | 2/2017 | Cronenberg ........ A61M 5/2459 |
| 2018/0207030 | A1 | 7/2018 | Kadalion |
| 2020/0022416 | A1* | 1/2020 | Alarcon ........... A61M 15/0028 |
| 2020/0138367 | A1 | 5/2020 | Liu |
| 2020/0215314 | A1 | 7/2020 | Wills et al. |
| 2020/0345545 | A1 | 11/2020 | Zhang |
| 2020/0360180 | A1 | 11/2020 | Stowe |
| 2021/0085887 | A1 | 3/2021 | Woodbine et al. |

* cited by examiner

LIQUID MEDICATION DISPENSING APPARATUS

TECHNICAL FIELD

The present disclosure relates to a medicinal dosing apparatus and, more particularly relates, to an apparatus for dispensing a medicament or pharmaceutical compound (e.g., a liquid eye-medication) in a controlled manner, on an ocular surface of a subject.

BACKGROUND

Pharmaceutical products are prescribed by physicians for treating patients suffering from an infection or other medical conditions. The pharmaceutical products may be in form of a topical spray, topical gel or ointment (for absorption through the skin), pills or tablets, dissolvable strips, and the like. Some of these pharmaceutical products are applicable for treating the patient suffering from an infection or other medical conditions involving an eye. For instance, a physician prescribes a medicated solution (or eye drops) for administering to the eye of the patient. For using the eye drops, the patient uses a medicine dropper or squeezable bottle to apply drops of the medication to the eye. In conventional methods, a patient is required to squeeze the bottle for extruding the medication out of the bottle. However, there may be inconsistency in dispensing the dosage amount by using such conventional methods, thus resulting in dispensing of either little or overdose of the medication than what is needed as a prescribed dosage. Further, patients prescribed pharmaceutical products are also often required to monitor a medication volume in order to see if there is a need to refill the medication. However, it is often not possible for patients to monitor the medication volume accurately when the medication is within an opaque bottle, as is the case for eye drops.

Therefore, there is a need for an apparatus for dispensing liquid medication in a controlled manner to overcome one or more limitations stated above in addition to providing other technical advantages.

SUMMARY

Various embodiments of the present disclosure an apparatus for dispensing a medicament (such as, a liquid eye-medication) in a controlled manner.

In an embodiment, a liquid medication dispensing apparatus is disclosed. The apparatus includes a housing including an inner cavity and a cap hingedly coupled to an upper portion of the housing. The cap is operable between an open position and a closed position. The apparatus includes a cartridge assembly configured to be inserted in the inner cavity. The cartridge assembly includes a support structure configured at a bottom portion of the cartridge assembly and a mounting platform disposed on the support structure. Further, the cartridge assembly includes a nozzle base configured at a top portion of the cartridge assembly. The nozzle base includes a nozzle. The cartridge assembly includes an intermediate body portion coupling the support structure and the nozzle base while maintaining a gap therebetween for securing a medication bottle between the nozzle base and the mounting platform. Further, the apparatus includes a control unit disposed in the housing. The control unit is configured to at least receive a first signal from a circuitry associated with a dispensing button mounted to the housing, upon detection of an input on the dispensing button, and provide a command signal to a drive mechanism of the cartridge assembly, for retrieving a liquid medication from the medication bottle and extrude the liquid medication through the nozzle.

In another embodiment, a liquid medication dispensing apparatus is disclosed. The apparatus includes a housing including an inner cavity and a cap hingedly coupled to an upper portion of the housing. The cap is operable between an open position and a closed position. A dispensing button is mounted to the upper portion of the housing. The apparatus includes a cartridge assembly configured to be inserted in the inner cavity. The cartridge assembly includes a support structure configured at a bottom portion of the cartridge assembly and a mounting platform disposed on the support structure. Further, the cartridge assembly includes a nozzle base configured at a top portion of the cartridge assembly. The nozzle base includes a nozzle. The cartridge assembly includes an intermediate body portion coupling the support structure and the nozzle base while maintaining a gap therebetween for securing a medication between the nozzle base and the mounting platform. The apparatus includes a control unit disposed in the housing. The control unit is configured to at least receive a first signal from a circuitry associated with the dispensing button, upon detection of an input on the dispensing button. The control unit is configured to determine, if the cap is operated in the open position, based on a second signal from a latch mechanism coupled to the housing and the cap. Based on determining the cap is operated in the open position, control unit provides a command signal to a drive mechanism of the cartridge assembly for retrieving a liquid medication from the medication bottle and extrude the liquid medication through the nozzle, for administering to an ocular surface of a subject.

In yet another embodiment, an ophthalmic liquid medication dispensing apparatus is disclosed. The apparatus includes a housing including an inner cavity and a cap hingedly coupled to an upper portion of the housing. The cap is operable between an open position and a closed position. A dispensing button is mounted to the upper portion of the housing. The apparatus includes a cartridge assembly configured to be inserted in the inner cavity. The cartridge assembly includes a support structure configured at a bottom portion of the cartridge assembly and a mounting platform disposed on the support structure. Further, the cartridge assembly includes a nozzle base configured at a top portion of the cartridge assembly. The nozzle base includes a nozzle. The cartridge assembly includes an intermediate body portion coupling the support structure and the nozzle base while maintaining a gap therebetween for securing a medication bottle between the nozzle base and the mounting platform. The cartridge assembly further includes a drive mechanism including a piston chamber. The piston chamber includes an inlet fluidically coupled to an opening of the medication bottle and an outlet fluidically coupled to the nozzle via a tube. The drive mechanism further includes a plunger disposed within the piston chamber and an actuator including a drive screw coupled to the plunger. The apparatus further includes a control unit disposed in the housing. The control unit is configured to at least receive a first signal from a circuitry associated with the dispensing button, upon detection of an input on the dispensing button. The control unit is configured to determine, if the cap is operated in the open position, based on a second signal from a latch mechanism coupled to the housing and the cap. Based on determining the cap is operated in the open position, the control unit provides a command signal to the drive mechanism, for retrieving a liquid medication from the medication bottle and extrude the liquid medication through the nozzle. Further, upon receipt of the command signal, the actuator operates the drive screw to drive the plunger between a first position and a second position within the piston chamber for receiving the liquid medication within the piston chamber via the inlet, and to extrude the liquid medication through the nozzle via the tube fluidically coupled to the outlet, respectively. The plunger operated between the first position and the second position creates a differential pressure within the piston chamber, which enables extruding of a metered volume of the liquid medication from the nozzle, for a predefined time. The liquid medication is an ophthalmic liquid medication, for administering to an ocular surface of a subject.

BRIEF DESCRIPTION OF THE FIGURES

The following detailed description of illustrative embodiments is better understood when read in conjunction with the appended drawings. For the purpose of illustrating the present disclosure, exemplary constructions of the disclosure are shown in the drawings. However, the present disclosure is not limited to a specific device or a tool and instrumentalities disclosed herein. Moreover, those in the art will understand that the drawings are not to scale. Wherever possible, like elements have been indicated by identical numbers.

Figure 1A:
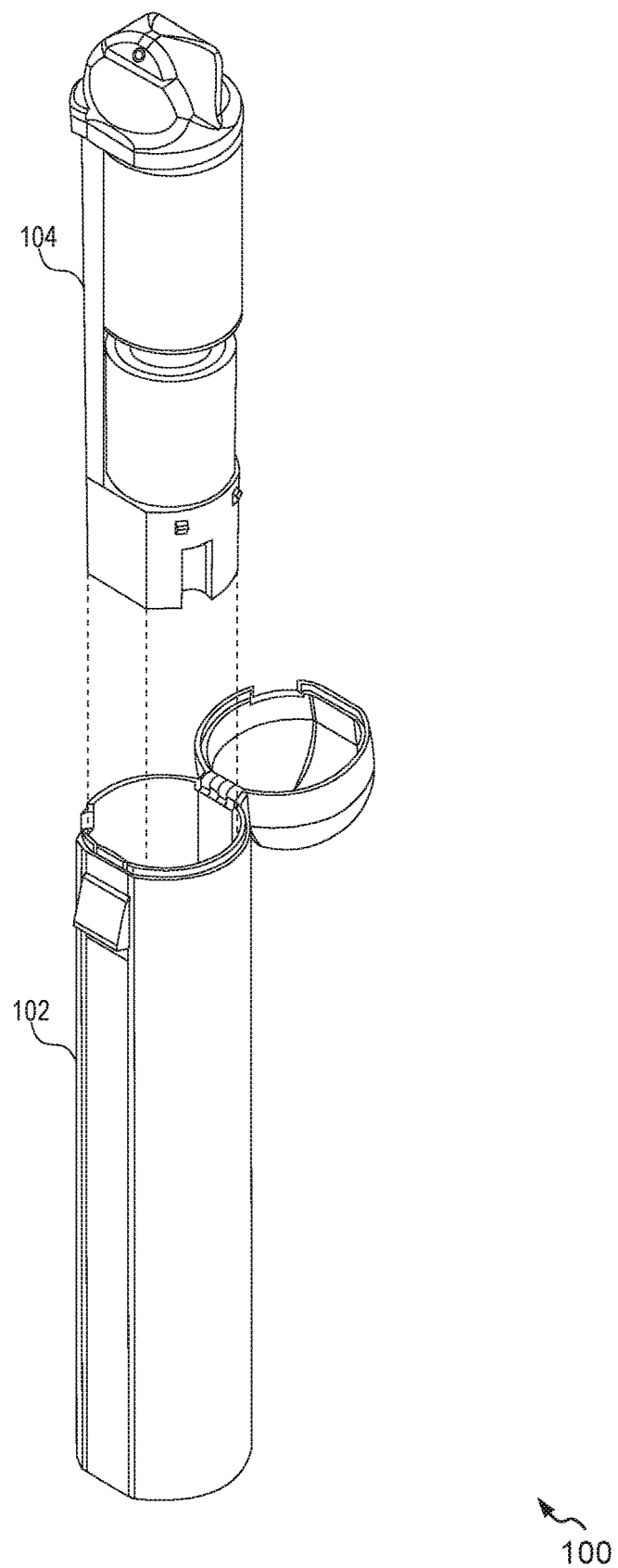
FIG. 1A illustrates an exploded view of a liquid medication dispensing apparatus, in accordance with an example embodiment of the present disclosure.

The drawings referred to in this description are not to be understood as being drawn to scale except if specifically noted, and such drawings are only exemplary in nature.

DETAILED DESCRIPTION

In the following description, for purposes of explanation, numerous specific details are set forth in order to provide a thorough understanding of the present disclosure. It will be apparent, however, to one skilled in the art that the present disclosure can be practiced without these specific details. Descriptions of well-known components and processing techniques are omitted to not obscure the embodiments herein unnecessarily. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Reference in this specification to "one embodiment" or "an embodiment" means that a particular feature, structure, or characteristic described in connection with the embodiment is included in at least one embodiment of the present disclosure. The appearances of the phrase "in an embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

Moreover, although the following description contains many specifics for the purposes of illustration, anyone skilled in the art will appreciate that many variations and/or alterations to said details are within the scope of the present disclosure. Similarly, although many of the features of the present disclosure are described in terms of each other, or in conjunction with each other, one skilled in the art will appreciate that many of these features can be provided independently of other features. Accordingly, this description of the present disclosure is set forth without any loss of generality to, and without imposing limitations upon, the present disclosure.

Overview

Various example embodiments of the present disclosure provide an apparatus for dispensing a medicament or pharmaceutical compound (such as a liquid eye medication or an ophthalmic liquid medication) in a controlled manner to an ocular surface of a subject. In an embodiment, the apparatus includes a housing including an inner cavity and a cap hingedly coupled to an upper portion of the housing. The cap is operable between an open position and a closed position. The apparatus includes a cartridge assembly configured to be inserted in the inner cavity. The cartridge assembly includes a mounting platform disposed on the support structure, a nozzle base including a nozzle and an intermediate body portion coupling the support structure and the nozzle base while maintaining a gap therebetween for securing a medication bottle between the nozzle base and the mounting platform. The cartridge assembly further includes a drive mechanism. The drive mechanism includes a piston chamber. The piston chamber includes an inlet fluidically coupled to an opening of the medication bottle and an outlet fluidically coupled to the nozzle via a tube. The drive mechanism further includes a plunger disposed within the piston chamber and an actuator including a drive screw coupled to the plunger.

In some embodiments, the apparatus includes a control unit disposed in the housing. The control unit is configured to receive a first signal from a circuitry associated with a dispensing button, upon detection of a press input on the dispensing button. Thereafter, the control unit determines, if the cap is operated in the open position, based on a second signal from a latch mechanism coupled to the housing and the cap. The latch mechanism temporarily engages the cap at an upper portion of the housing, when the cap is operated to the closed position. Based on determining the cap is operated in the open position, the control unit provides a command signal to the drive mechanism. Upon receipt of the command signal, the actuator operates the drive screw to drive the plunger between a first position and a second position within the piston chamber for receiving the liquid medication within the piston chamber via the inlet, and to extrude the liquid medication through the nozzle via the tube fluidically coupled to the outlet, respectively. The plunger operated between the first position and the second position creates a differential pressure within the piston chamber, which enables extruding of a metered volume of the liquid medication from the nozzle, for a predefined time.

Various embodiments of the present invention are described hereinafter with reference to FIGS. 1A-1C to FIG. 8.

FIG. 1A illustrates an exploded view of a liquid medication dispensing apparatus 100, in accordance with an example embodiment of the present disclosure. The liquid medication dispensing apparatus 100 (hereinafter interchangeably referred to as 'the apparatus 100') is configured to dispense ophthalmic liquid medication to an ocular surface (see, 702 of FIG. 7) of a subject (see, 700 of FIG. 7). The apparatus 100 includes a housing 102 (as shown in FIG. 1B) and a cartridge assembly 104 (as shown in FIG. 1C).

The housing 102 is configured to provide structural support to one or more components of the housing 102. The cartridge assembly 104 is configured to receive a medication bottle containing the ophthalmic liquid medication. The cartridge assembly 104 includes mechanisms for extruding the ophthalmic liquid medication from the apparatus 100, for administering to the subject 700. The mechanisms and the components associated with the cartridge assembly 104 for dispensing the liquid medication are herein explained with reference to FIG. 4.

Figure 1B:
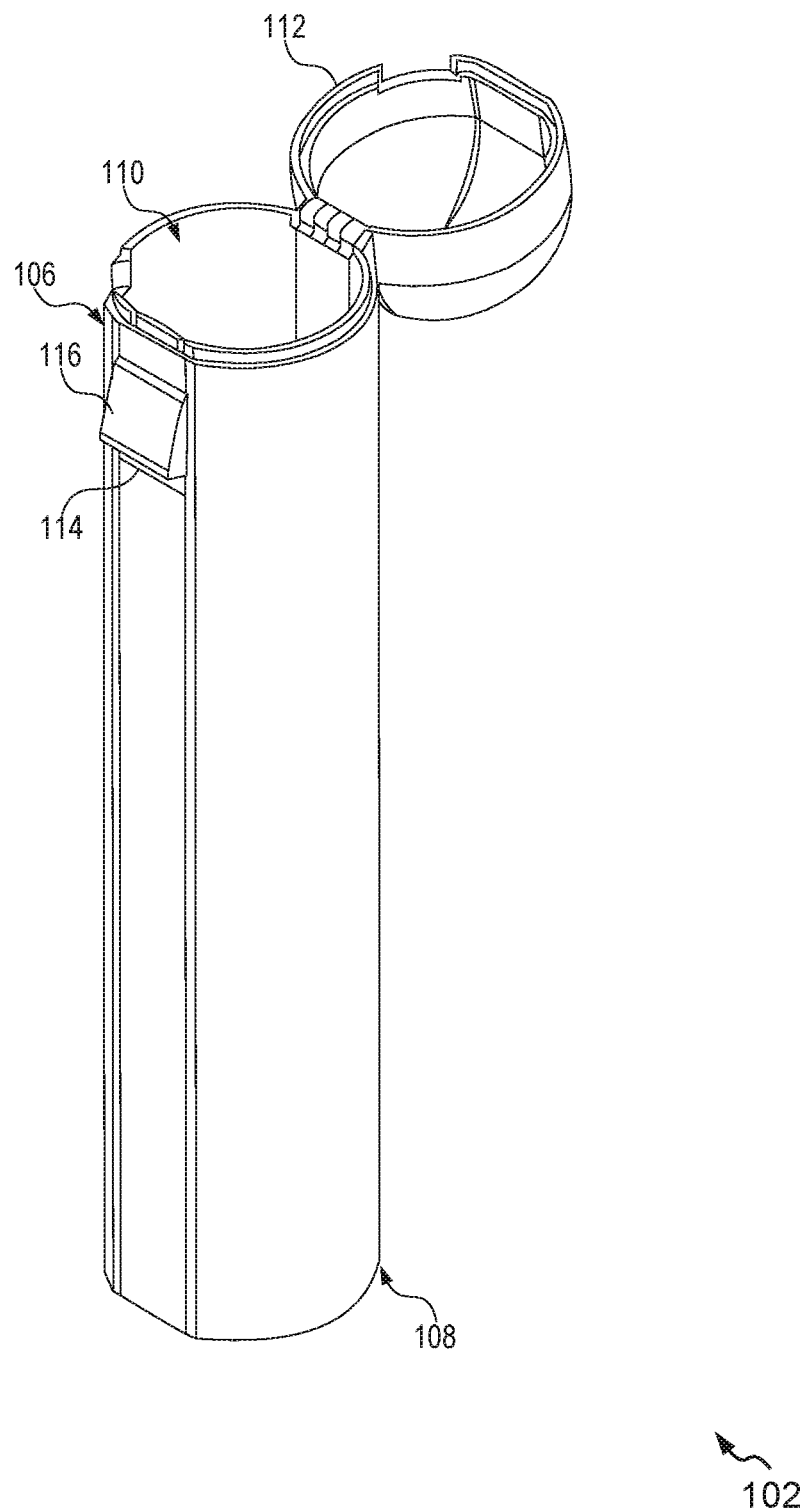
FIG. 1B illustrates a schematic view of a housing of the liquid medication dispensing apparatus, in accordance with an example embodiment of the present disclosure.
Figure 1C:
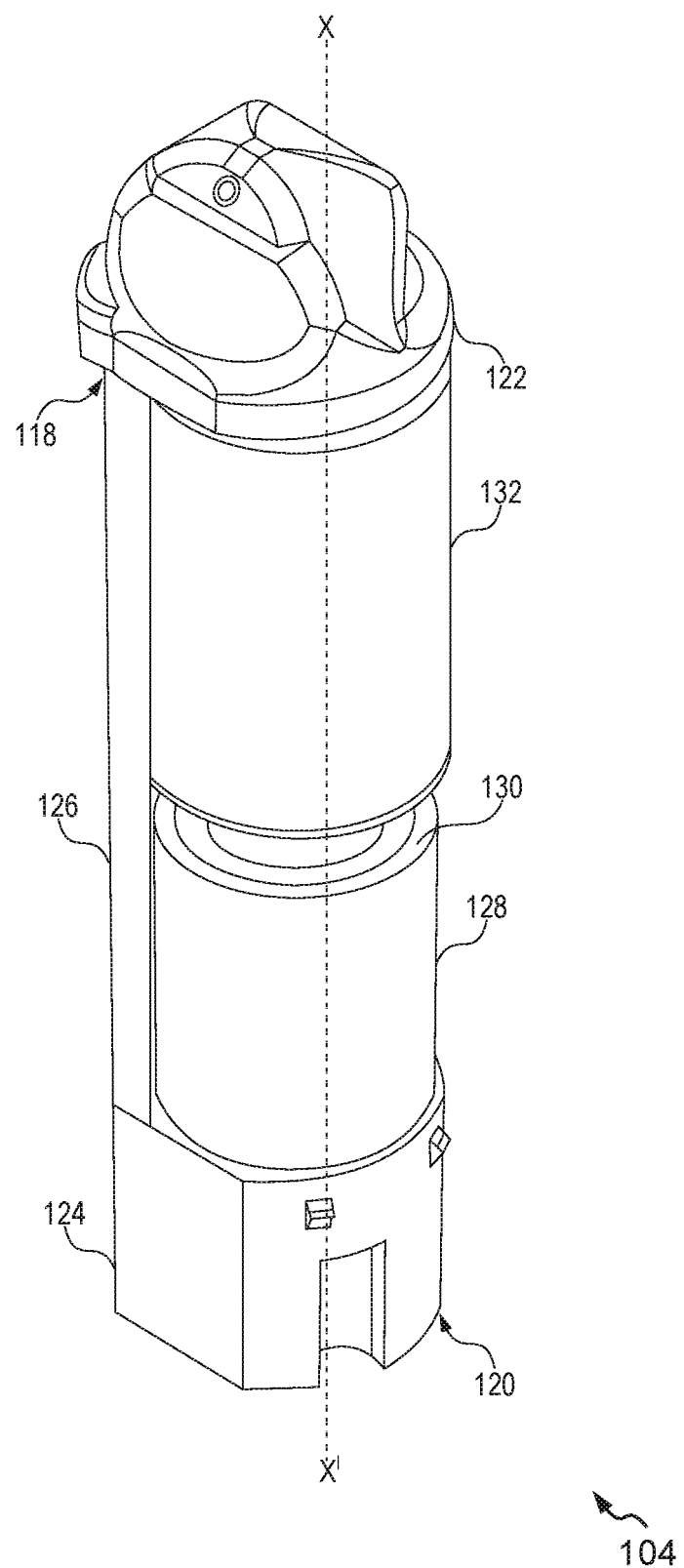
FIG. 1C illustrates a schematic view of a cartridge assembly of the liquid medication dispensing apparatus, in accordance with an example embodiment of the present disclosure.

The housing 102 includes an upper portion 106 and a lower portion 108 (as shown in FIG. 1B). The housing 102 includes an inner cavity 110 (as shown in FIG. 1B). The inner cavity 110 is adapted to receive the cartridge assembly 104 in a sliding manner. As shown in FIG. 1B, the housing 102 is configured to be a substantially cylindrical geometry body. Alternatively, the housing 102 is configured with a square geometry body or any other geometry as per design feasibility and requirement. Further, the housing 102 including the inner cavity 110 is dimensioned in conformity with the dimension of the cartridge assembly 104, so as to snuggly receive the cartridge assembly 104 when inserted therein. The housing 102 is made of material that provides a barrier to water and dust ingress. In an embodiment, the housing 102 may be made of thermoplastic and amorphous polymer such as polycarbonate plastic (PC), Acrylonitrile Butadiene Styrene (ABS), and the like. The housing 102 made of thermoplastic and amorphous polymer materials may have a shelf-life with an intended use of up to 36 months.

The housing 102 includes a cap 112 hingedly coupled at the upper portion 106 of the housing 102 (as shown in FIG. 1B). The cap 112 is operable between an open position (see, 302 of FIG. 3A) and a closed position (see, 306 of FIG. 3C). Further, the housing 102 includes a cut-out portion 114 configured along a length of the housing 102. The apparatus 100 includes a dispensing button 116 mounted to the housing 102 and positioned proximate to the upper portion 106 of the housing 102 (as shown in FIG. 1B). The dispensing button 116 enables the subject 700 to press the dispensing button 116 to express the liquid medication from the apparatus 100.

Additionally, the housing 102 is configured to provide structural support for electrical circuitry and various connectors for connecting the electrical components associated with the apparatus 100 which will be explained further in detail.

The cartridge assembly 104 is designed to be inserted in the inner cavity 110. Mounting the cartridge assembly 104 within the housing 102 is herein explained in detail with references to FIGS. 3A-3C. The cartridge assembly 104 includes a nozzle base 122, a support structure 124 and an intermediate body portion 126 (as shown in FIG. 1C). The intermediate body portion 126 couples the nozzle base 122 and the support structure 124, while maintaining a gap therebetween. In an embodiment, the intermediate body portion 126, the nozzle base 122 and the support structure 124 may be detachably coupled to each other to form the cartridge assembly 104. As shown in FIG. 1C, the nozzle base 122 and the support structure 124 are configured at a top portion 118 and a bottom portion 120 of the cartridge assembly 104. In other words, the nozzle base 122 corresponds to a top housing of the cartridge assembly 104 and the support structure 124 corresponds to a bottom housing of the cartridge assembly 104.

The cartridge assembly 104 further includes a mounting platform 128 (as shown in FIG. 1C). The mounting platform 128 is secured and/or disposed on the support structure 124. The mounting platform 128 includes a groove 130 configured along a length of the mounting platform 128. The mounting platform 128 facilitates the insertion of a medication bottle 132 containing the liquid medication therein (as shown in FIG. 1C). The medication bottle 132 is mounted to the mounting platform 128, and the support structure 124 and the nozzle base 122 are aligned along an axis X-X' of the cartridge assembly 104 (as shown in FIG. 1C). Securing the medication bottle 132 within the cartridge assembly 104 is herein explained in detail with references to FIGS. 2A-2B.

The cartridge assembly 104 may be made of thermoplastic materials such as, but not limited to, polypropylene (PP). Generally, the aforementioned materials used for fabricating the cartridge assembly 104 include properties such as safe for direct contact with the medication, recyclable, and simple to mold into desired shapes. Further, the cartridge assembly 104 is disposable with intended use of about 30 days and contains electronic circuitry for dispensing the medication therefrom.

Figure 2A:
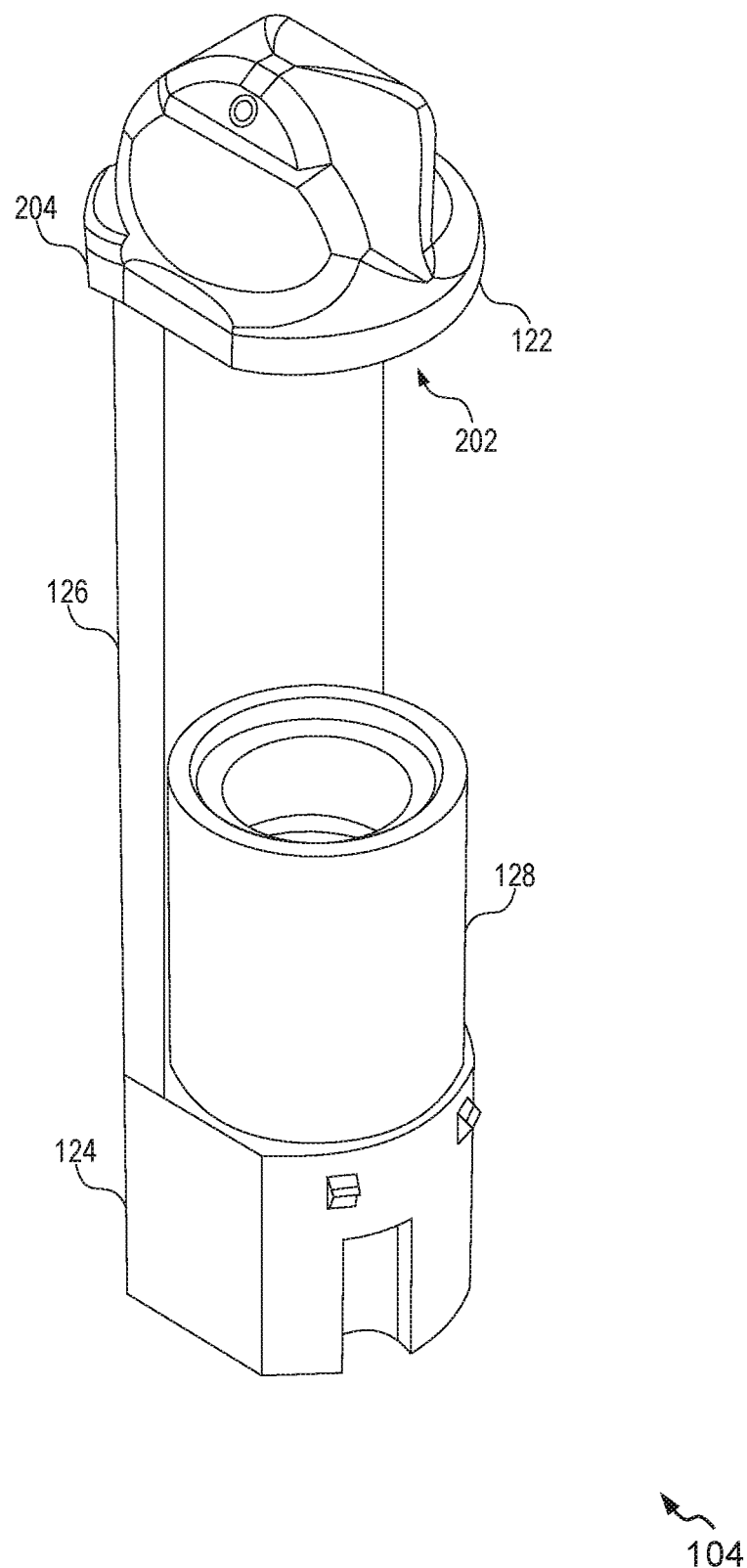
FIGS. 2A-2B illustrate a step-by-step process for securing a medication bottle to the cartridge assembly, in accordance with an example embodiment of the present disclosure.
Figure 2B:
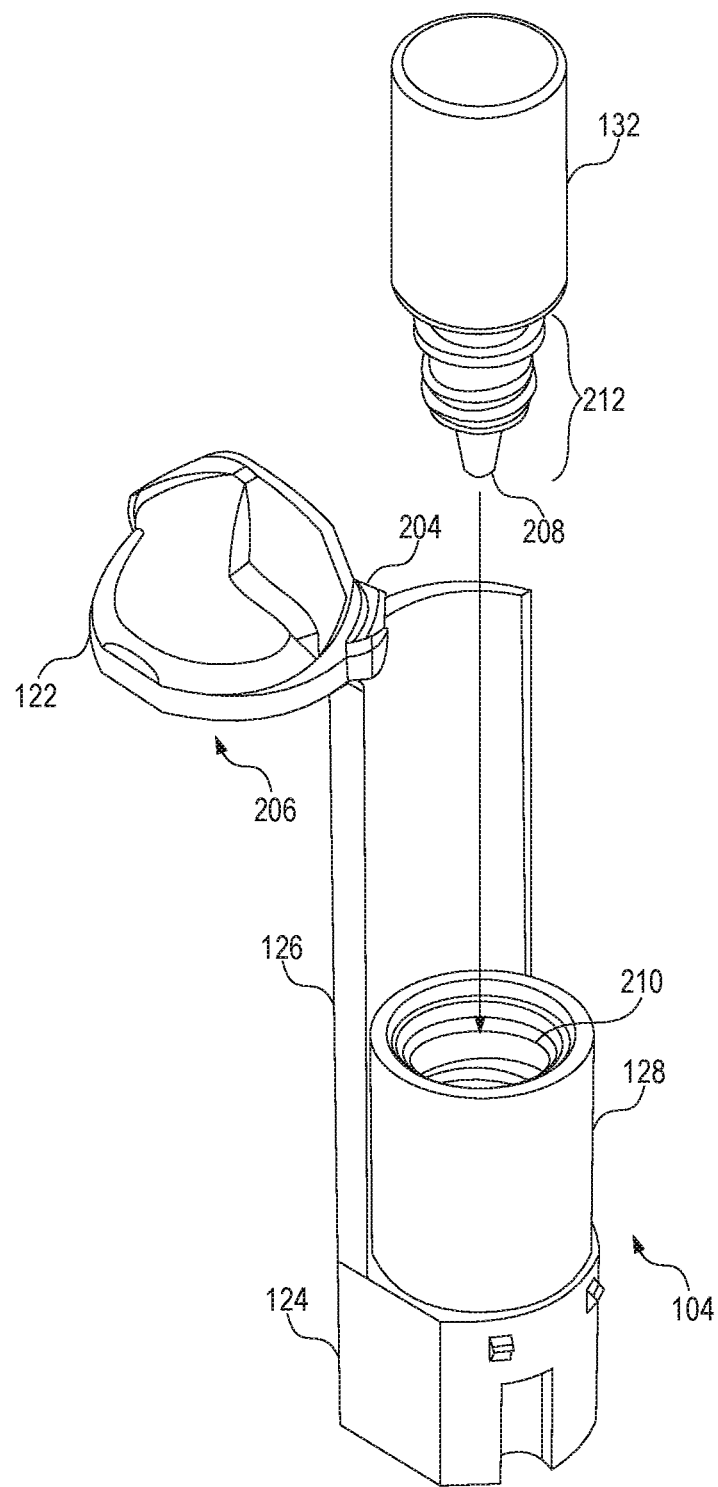

FIGS. 2A-2B illustrate a step-by-step process for securing the medication bottle 132 to the cartridge assembly 104, in accordance with an example embodiment of the present disclosure. As shown in FIG. 2A, the cartridge assembly 104 is shown where the nozzle base 122 is operated in a locked state 202. For securing the medication bottle 132 to the cartridge assembly 104, the nozzle base 122 is twisted for allowing the medication bottle 132 to be inserted into the mounting platform 128 (as shown in FIG. 2B). In other words, the nozzle base 122 is operated to an unlocked state (see, 206 of FIG. 2B). It should be understood that the nozzle base 122 is pivotally mounted to the intermediate body portion 126 and positioned at the top portion 118. More specifically, the nozzle base 122 includes a fastening member 204 secured to one end of the nozzle base 122. The fastening member 204 allows the nozzle base 122 to be pivotally mounted to the intermediated body portion 126.

The nozzle base 122 is operable between the locked state 202 and the unlocked state 206 due to pivotal movement of the nozzle base 122. The fastening member 204 may include a lock mechanism (not shown in Figures) to prevent the nozzle base 122 beyond the locked state 202 and the unlocked state 206. Further, the nozzle base 122 operated to the unlocked state 206 facilitates space for easy insertion of the medication bottle 132. More specifically, the medication bottle 132 is aligned in an upright position such that an opening 208 of the medication bottle 132 is oriented towards the mounting platform 128. Upon aligning, the medication bottle 132 is secured to the mounting platform 128 of the mounting platform 128 (as shown in FIG. 1C).

In one configuration, the mounting platform 128 may include a plurality of threads 210 configured in the groove 130 (as shown in FIG. 2B). The threads 210 may be selected based on the shape of a tip portion 212 of the medication bottle 132. In this configuration, the medication bottle 132 may be secured to the groove 130 by rotating the medication bottle 132 until the medication bottle 132 is screwed into the groove 130, thus enabling a snug fit of the medication bottle 132. As shown, the medication bottle 132 is secured between the nozzle base 122 and the mounting platform 128. In another configuration, the medication bottle 132 may be secured to the groove 130 using a snap-fit mechanism, or any other fastening mechanism as per design feasibility and requirement.

It should be understood that the shape and dimensions of the groove 130 of the mounting platform 128 are configured in conformity with the shape and dimension of the tip portion 212 of the medication bottle 132 for snuggly securing the medication bottle 132 therein. Additionally, the apparatus 100 includes a cartridge gasket (see, 426 of FIG. 4A) disposed in the cartridge assembly 104. The cartridge gasket 426 enables an airtight seal between the medication bottle 132 and the mounting platform 128.

Upon securing the medication bottle 132 to the mounting platform 128, the nozzle base 122 is operated to the locked state 202 (as shown in FIG. 1C). In this scenario, the support structure 124, the medication bottle 132, and the nozzle base 122 are aligned along the axis X-X'.

Figure 3A:
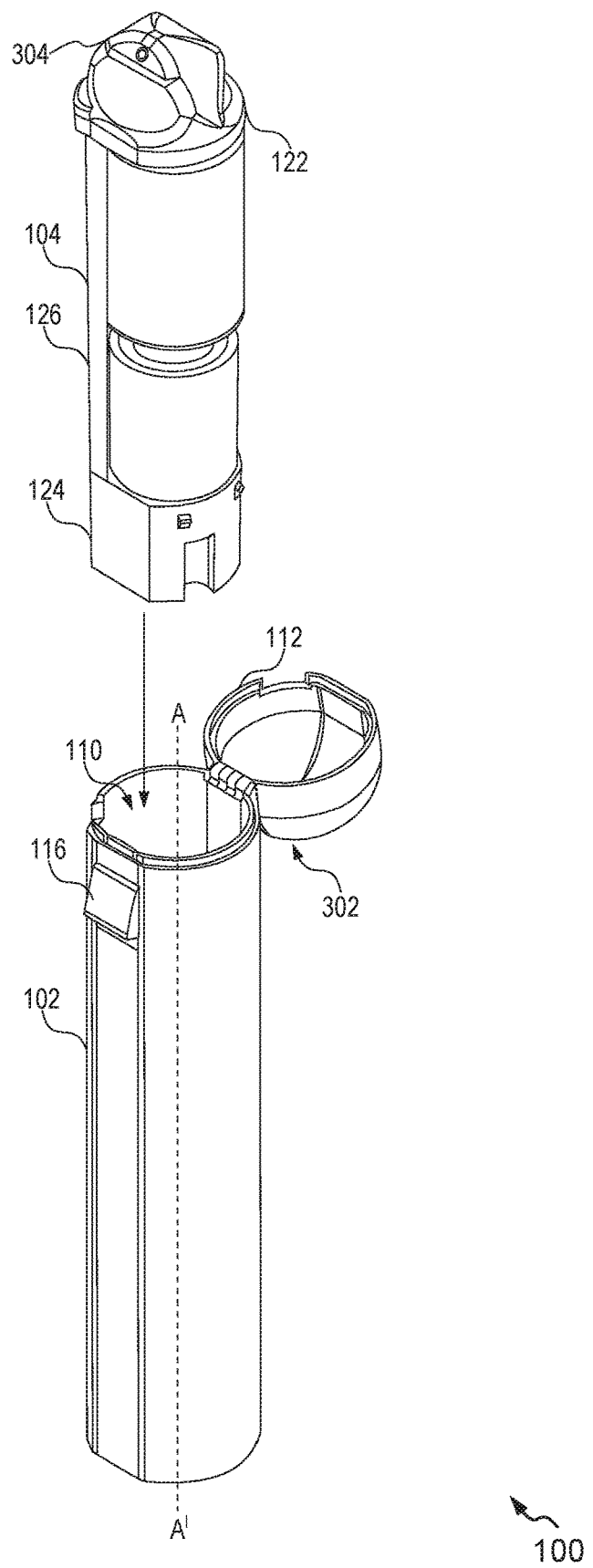
FIGS. 3A-3C illustrate a step-by-step process for securing the cartridge assembly within the housing, in accordance with an example embodiment of the present disclosure.
Figure 3B:
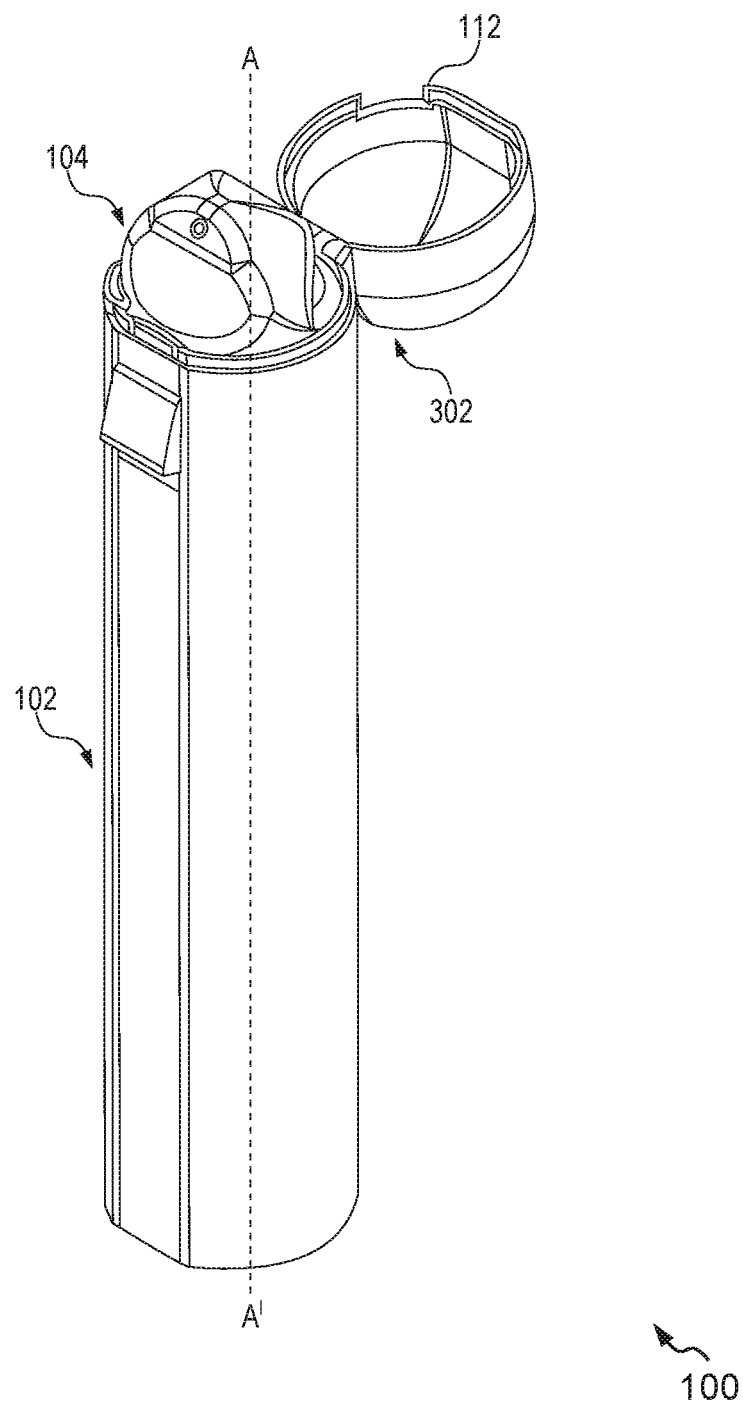
Figure 3C:
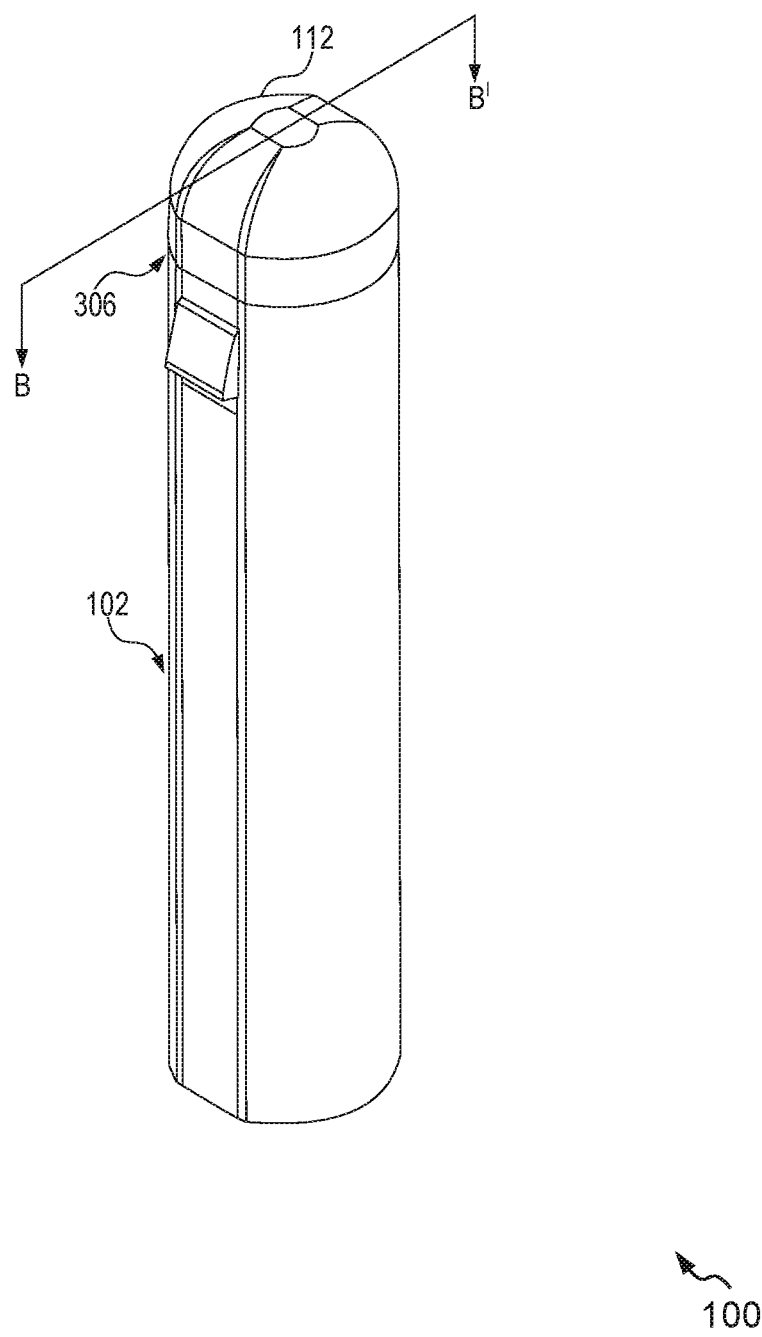

FIGS. 3A-3C illustrate a step-by-step process for securing the cartridge assembly 104 within the housing 102, in accordance with an example embodiment of the present disclosure. As shown in FIG. 3A, the cartridge assembly 104 is aligned along an axis A-A' of the housing 102. The axis A-A' corresponds to a central axis of the housing 102. In this scenario, the cap 112 is operated in the open position 302 for receiving the cartridge assembly 104. Thereafter, the cartridge assembly 104 is secured within the inner cavity 110 by sliding the cartridge assembly 104 within the inner cavity 110 until the cartridge assembly 104 is fully inserted in the housing 102 (as shown in FIG. 3B). It is noted that the nozzle base 122 extends beyond the upper portion 106 of the housing 102 for dispensing the liquid medication (as shown in FIG. 3B).

Prior to securing the cartridge assembly 104, a nozzle 304 configured in the nozzle base 122 is aligned in line with the dispensing button 116 on the housing 102. This alignment facilitates extruding the liquid medication through the nozzle 304 based on providing an input (i.e. a press input) on the dispensing button 116 which will be explained further in detail. Further, the cap 112 may be operated in the closed position 306 (as shown in FIG. 3C).

Figure 4A:
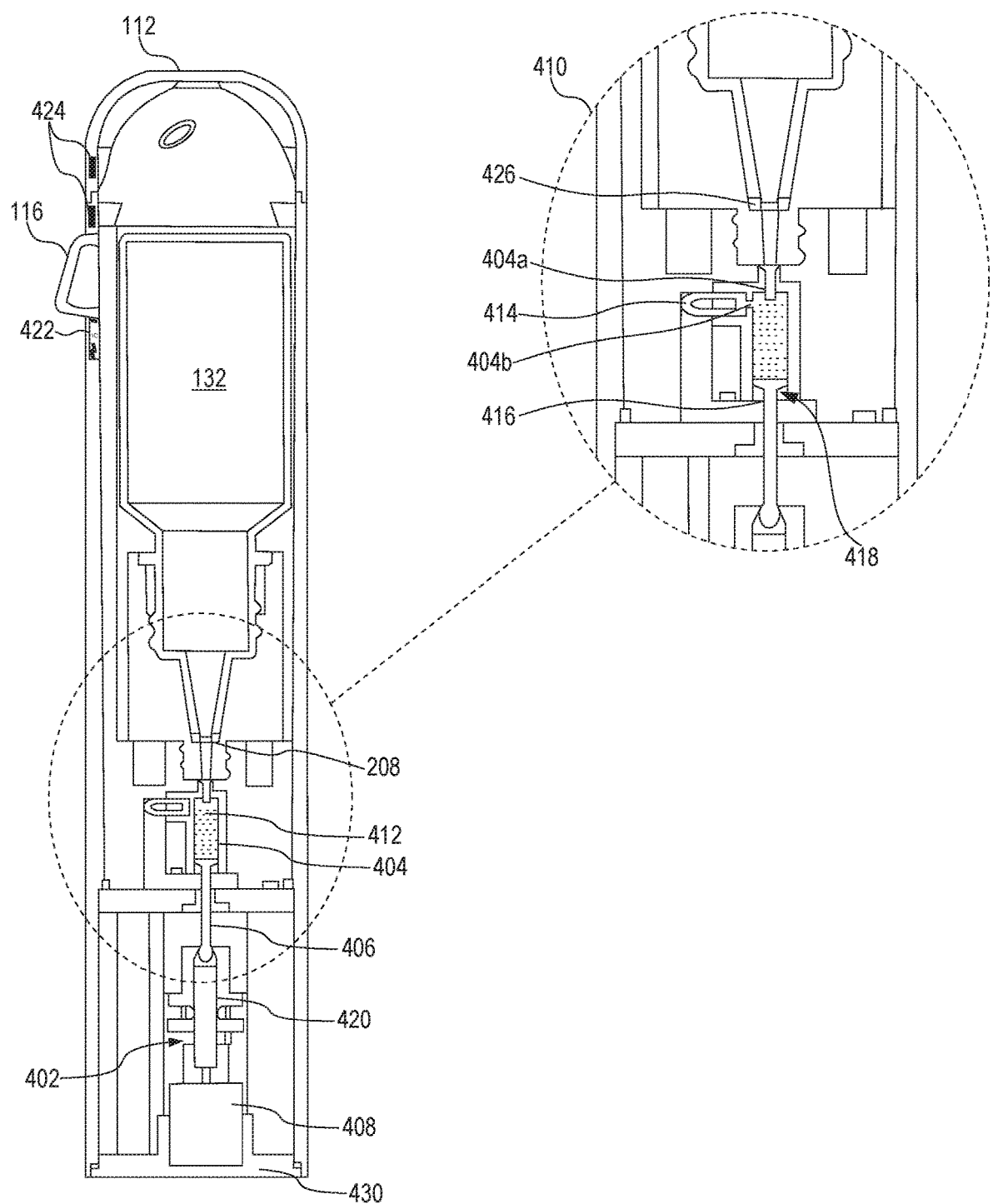
FIG. 4A illustrates a cross-sectional view of the apparatus, depicting a plunger operated in a first position within a piston chamber of the cartridge assembly, in accordance with an example embodiment of the present disclosure.

Referring to FIG. 4A in conjunction with FIG. 3C, a cross-sectional view of the apparatus 100 along an axis B-B' of the apparatus 100 is illustrated, in accordance with an example embodiment of the present disclosure. As show in FIG. 4A, the apparatus 100 includes a drive mechanism 402. The drive mechanism 402 is coupled to the medication bottle 132 and configured to retrieve a liquid medication 412 (exemplarily represented in dashed lines) from the medication bottle 132 and extrude the liquid medication through the nozzle 304.

Figure 5:
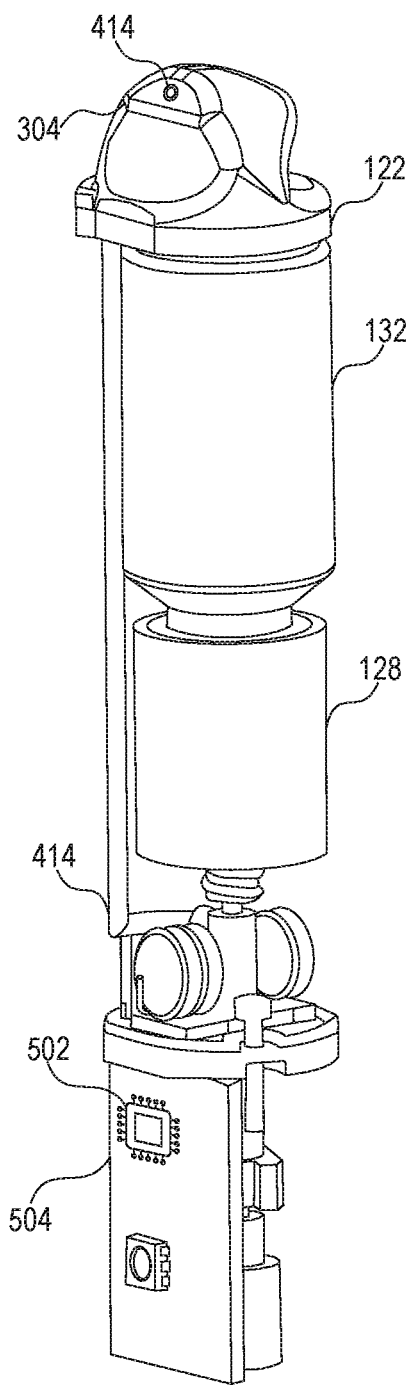
FIG. 5 illustrates a schematic view of an internal configuration of the apparatus, depicting a control unit mounted to an internal side panel of the housing, in accordance with an example embodiment of the present disclosure.

The drive mechanism 402 includes a piston chamber 404, a plunger 406 and an actuator 408. The piston chamber 404 includes an inlet 404a and an outlet 404b (see, an enlarged portion 410). The piston chamber 404 is positioned in line with the opening 208 of the medication bottle 132, so as to receive the liquid medication 412 from the medication bottle 132 through the inlet 404a. In other words, the inlet 404a of the piston chamber 404 is fluidically coupled to the opening 208 of the medication bottle 132. Further, the outlet 404b of the piston chamber 404 is fluidically coupled to a tube 414. The tube 414 is fluidically coupled to the nozzle 304 for extruding the liquid medication 412 stored within the piston chamber 404 through the nozzle 304 (as shown in FIG. 5).

Further, the piston chamber 404 includes a passageway 416 for receiving the plunger 406 therein (see, the enlarged portion 410). In other words, the plunger 406 is disposed within the piston chamber 404. The plunger 406 may be made of materials such as, metals (e.g., steel), rubber, silicone or any other materials, or any combination thereof as per the design feasibility and requirement. In one configuration, the plunger 406 may be made of metals (e.g., steel) over-molded in rubber or silicone. In this configuration, the metal provides compressive and tensile strength, and the rubber/silicone provides the seal for moving in the piston chamber 404 which is explained further in detail. The plunger 406 is coupled to the actuator 408. More specifically, the actuator 408 includes a drive screw 420 which is coupled to the plunger 406. The plunger 406 is configured to create a differential pressure within the piston chamber 404 based on the operation of the actuator 408 and the drive screw 420. In an embodiment, the actuator 408 may be a rotating device (e.g., direct current (DC) motor) that is configured to provide a rotational movement, upon actuation. The rotatory movement may be translated to a linear movement by the drive screw 420 for operating the plunger 406 which will be explained further in detail.

The apparatus 100 further includes a circuitry 422 electronically coupled to the dispensing button 116. The circuitry 422 is configured to monitor the input provided on the dispensing button 116 for dispensing the liquid medication 412. More specifically, the circuitry 422 may include one or more electronic components for providing a first signal upon giving the press input on the dispensing button 116.

Further, the apparatus 100 includes a latch mechanism 424 mounted to the housing 102 and the cap 112. The latch mechanism 424 is configured to temporarily engage the cap 112, when the cap 112 is operated in the closed position 306. For example, the latch mechanism 424 may include magnetic material that is mounted to a portion of the housing 102 where the cap 112 rests in the closed position 306. As such, the latch mechanism 424 enables temporarily engaging the cap 112 (i.e. due to magnetic force of attraction of the housing 102 and the cap 112), when the cap 112 is operated in the closed position 306. Additionally, the latch mechanism 424 may be configured to generate a second signal, when the cap 112 is operated in the closed position 306.

The apparatus 100 further includes a control unit 502 disposed within the housing 102 (as shown in FIG. 5). As shown, the control unit 502 is mounted to an internal side panel 504 (as shown in FIG. 5). It should be noted that the internal side panel 504 is an integral component of the housing 102 that is configured to house the control unit 502. The control unit 502 is configured to operate the apparatus 100 for dispensing the liquid medication 412. More specifically, the control unit 502 is communicably coupled to the latch mechanism 424 associated with the cap 112, the circuitry 422 associated with the dispensing button 116 and the drive mechanism 402 of the cartridge assembly 104.

The control unit 502 is configured to operate the drive mechanism 402 for dispensing the liquid medication 412. More specifically, the control unit receives the first signal from the circuitry 422 associated with the dispensing button 116. As explained above, the first signal is transmitted by the circuitry 422 based on providing the press input on the dispensing button 116. In other words, the circuitry 422 may include conductive strip within the dispensing button 116 which bridges the circuit when the dispensing button 116 is pressed.

Upon receipt of the first signal, the control unit 502 checks if the cap 112 is operated in the closed position 306. More specifically, the control unit 502 is configured to check the second signal coming from the latch mechanism 424. In one case, if the second signal is being transmitted to the control unit 502 from the latch mechanism 424, the cap 112 is determined to be operated in the closed position 306. In another case, the cap 112 is determined to be operated in the open position 302 due to the absence of the second signal from the latch mechanism 424. This enables the restriction for dispensing the liquid medication 412 from the apparatus 100, and prevents wastage of the liquid medication 412.

Thereafter, the control unit 502 transmits a command signal to the drive mechanism 402. The command signal operates the drive mechanism 402 to collect the liquid medication 412 within the piston chamber 404 and extrude the liquid medication 412 through the nozzle 304.

More specifically, upon receipt of the command signal, the actuator 408 provides rotatory motion in a specific direction (e.g., clock-wise direction). The rotatory movement of the actuator 408 is translated to the linear movement through the drive screw 420 of the actuator 408. The linear movement enables the plunger 406 to be operated between a first position 418 and a second position (see, 428 of FIG. 4B). The plunger 406 operable between the first position 418 and the second position 428 corresponds to one cycle of dispensing of the liquid medication 412.

Figure 4B:
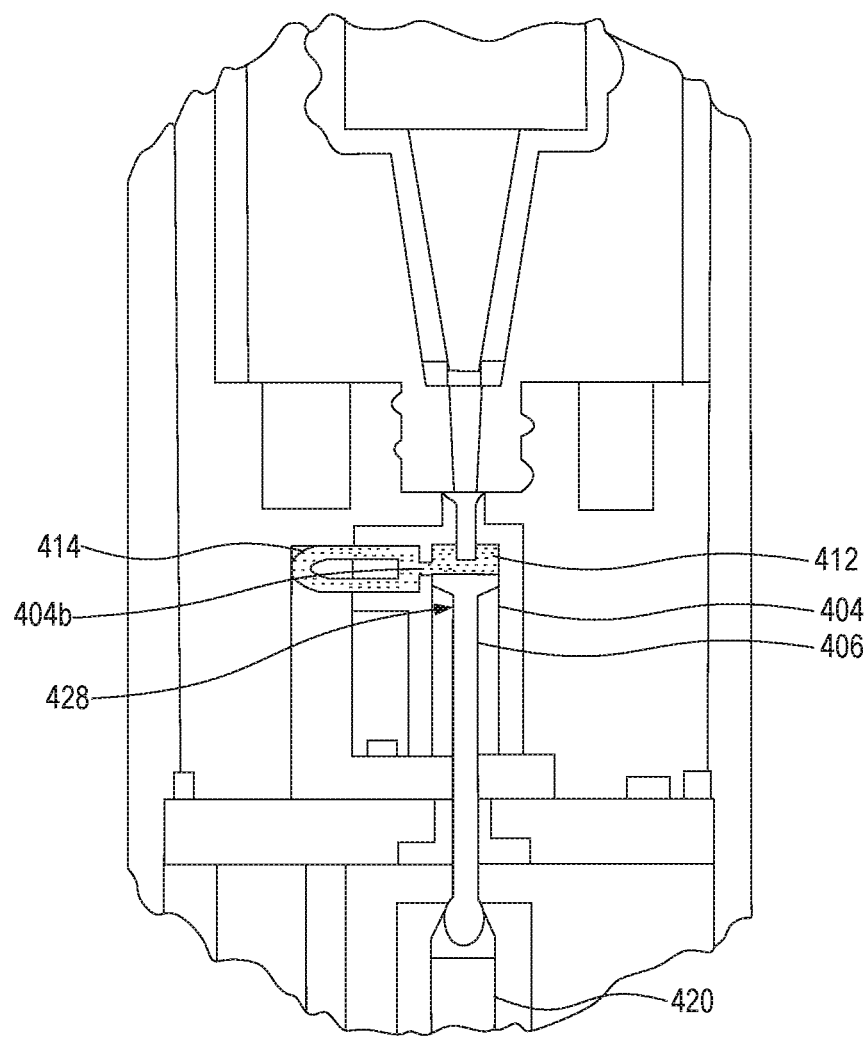
FIG. 4B illustrates a cross-sectional view of a portion of the apparatus, depicting the plunger operated in the second position within the piston chamber of the cartridge assembly, in accordance with an example embodiment of the present disclosure.

Upon receipt of the command signal, the plunger 406 is pushed into the piston chamber 404 (i.e. from the first position 418 to the second position 428) for extruding the liquid medication 412 collected in the piston chamber 404. In particular, the plunger 406 is operated to the second position 428 by pushing the plunger 406 further into the piston chamber 404. The plunger 406 operated in the second position 428 causes a greater pressure within the piston chamber 404 than in the tube 414, thus forcing and/or extruding the liquid medication 412 from the piston chamber 404 through the outlet 404b (as shown in FIG. 4B). Thereafter, the liquid medication 412 enters the tube 414 through the outlet 404b and is dispensed through the nozzle 304.

Consequently, the plunger 406 is operated to the first position 418 from the second position 428 for receiving the liquid medication 412 for the next extrusion. More specifically, the control unit 502 determines that the drive screw 420 has rotated enough and the liquid medication 412 has been dispensed from the apparatus 100. Upon determining, the control unit 502 reverses the power to the actuator 408. Reversing of the power allows the actuator 408 to rotate in the direction opposite to that of the direction when the plunger 406 is operated to the second position 428 from the first position 418. Similarly, the rotatory movement is translated to the linear movement through the drive screw 420, which enables the plunger 406 to be pulled outward from the piston chamber 404 (i.e. from the second position 428 to the first position 418). In this scenario, a lower pressure is created within the piston chamber 404 than in the medication bottle 132, which enables the medication bottle 132 to dispense the liquid medication 412 into the piston chamber 404 through the inlet 404a for next extrusion (as shown in FIG. 4A).

Additionally, the apparatus 100 may include an accelerometer (not shown in Figures) for monitoring an orientation angle of the apparatus 100, while dispensing the liquid medication 412. This mitigates the risk of dispensing air instead of actual dosage of the liquid medication 412.

It should be understood that the apparatus 100 is configured to dispense a metered volume of the liquid medication 412 from the nozzle 304, for a predefined time. More specifically, the plunger 406 operated between the first position 418 and the second position 428 creates a differential pressure within the piston chamber 404, which enables extruding of the metered volume of the liquid medication 412 for a predefined time. The plunger 406 operable between the first position 418 and the second position 428 corresponds to a stroke length. Thus, it is evident that the predefined time and the volume of the liquid medication 412 dispensed at each instance (i.e. upon the press input on the dispensing button 116) depend on the stroke length of the plunger 406. For example, the predefined time maybe 2 seconds and the metered volume may be 40 microliters (uL). The metered volume may vary with a threshold of plus/minus 5 microlitres (uL). The metered volume (e.g., 40 uL) and the predefined time (e.g., 2 seconds) may be standardized for the apparatus 100 to set to allow for the appropriate drug concentration to be delivered and absorbed for maximal treatment effect. In other words, the rate of the liquid medication extrusion is controlled so that liquid medication 412 is delivered over 2 seconds.

It should be noted that the dispensing of the metered volume of the liquid medication for the predefined time is independent of a time period of press input provided on the dispensing button 116 and the number of press inputs provided on the dispensing button 116 within the predefined time following the initial press input on the dispensing button 116. Additionally, the predefined time and the metered volume of the liquid medication 412 do not vary due to viscosity, density, form of matter, or any other physical characteristic of the liquid medication 412.

Further, the control unit 502 may be configured to compute one or more parameters related to a liquid medication volume upon each dispensing, and number of days of medication remaining within the medication bottle 132. For instance, the control unit 502 receives input information from the subject 700 or a remote server system communicably coupled to the control unit 502. The input information includes an initial medication volume available in the cartridge assembly 104.

Figure 6:
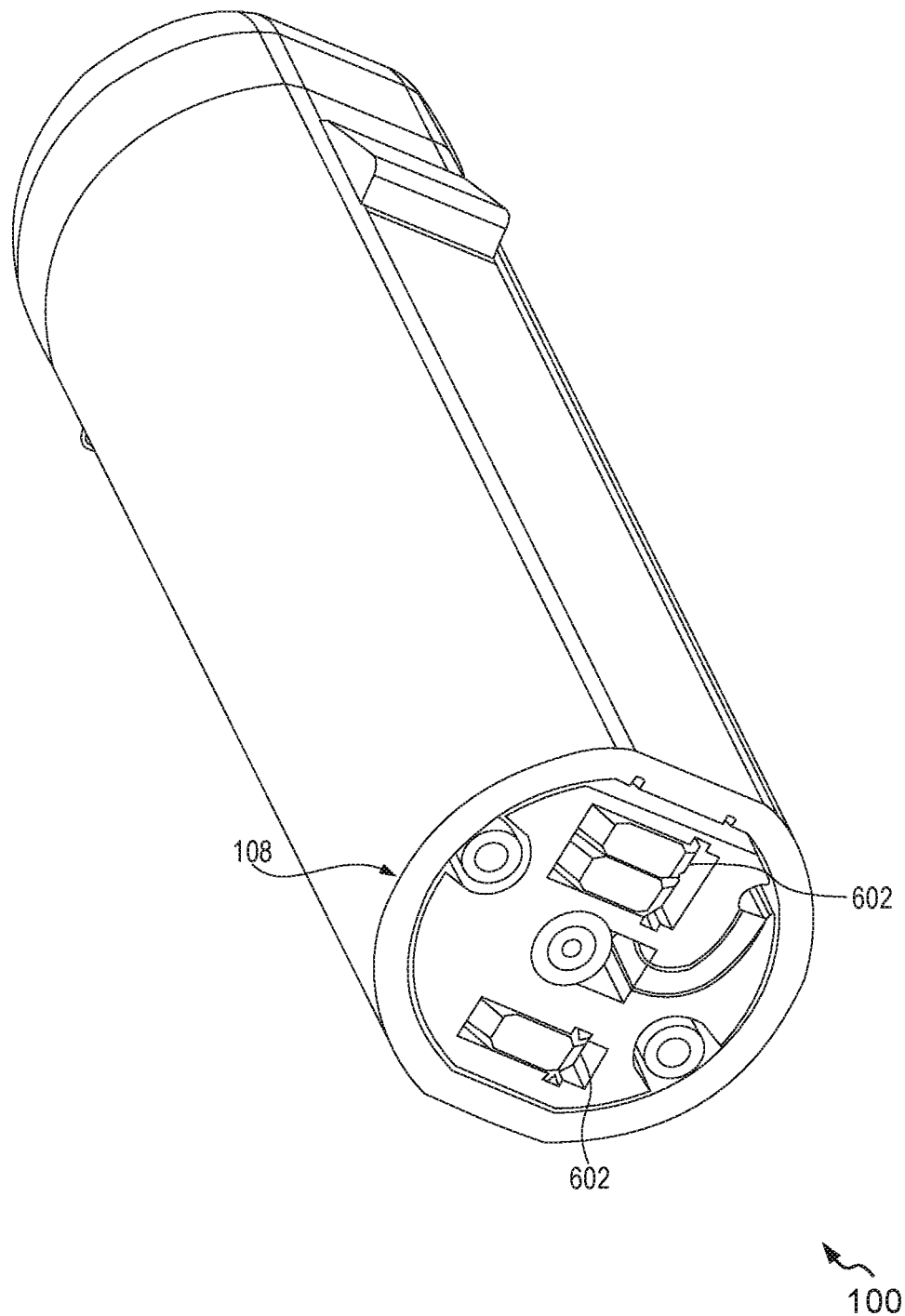
FIG. 6 illustrates a bottom perspective view of the apparatus, in accordance with an example embodiment of the present disclosure.

Further, it should be understood that the electronic components such as, the control unit 502, the circuitry 422, the latch mechanism 424, the actuator 408, and the like are powered for operating the apparatus 100. The apparatus 100 includes a battery (see, 602 of FIG. 6) mounted within the cartridge assembly 102 proximate to the bottom portion 120. The battery 602 provides power supply to the aforementioned electronic components. For example, the battery 602 may be a rechargeable battery or a non-rechargeable battery. The battery 602 is covered using a housing gasket (see, 430 of FIG. 4A) mounted at the lower portion 108 of the housing 102.

Figure 7:
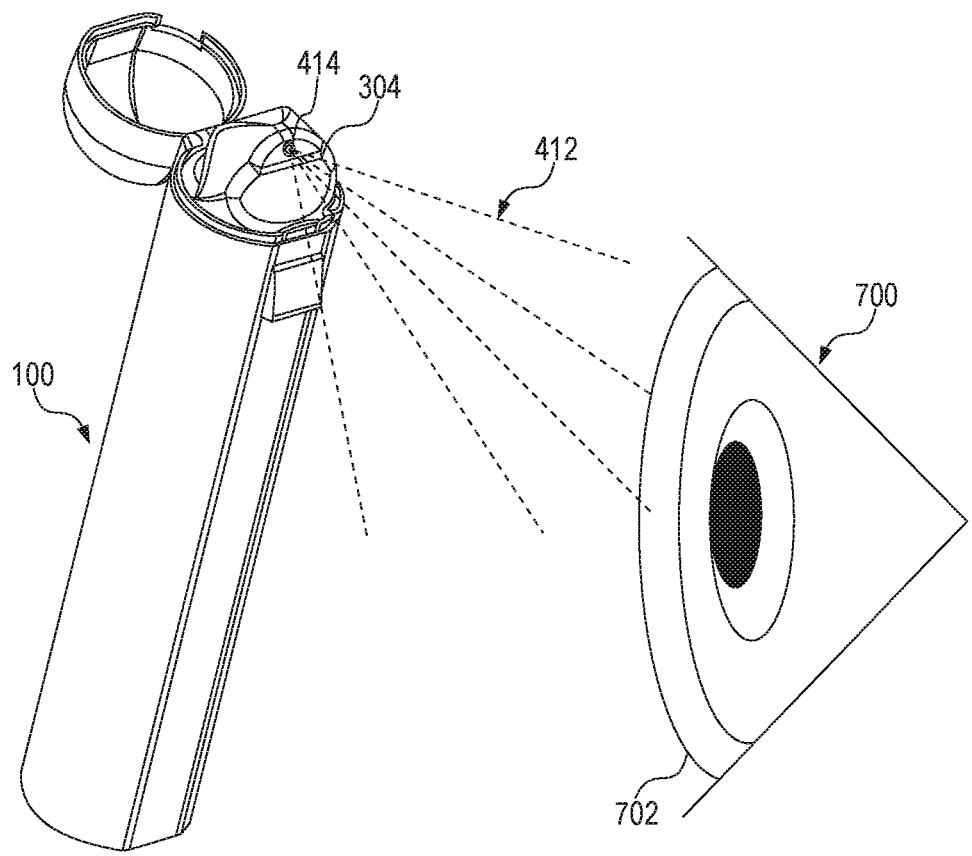
FIG. 7 illustrates dispensing of the liquid medication from the apparatus over an ocular surface of a subject, in accordance with an example embodiment of the present disclosure.

FIG. 7 in one exemplary embodiment of the present disclosure, illustrates dispensing the liquid medication 412 from the apparatus 100 over the ocular surface 702 of the subject 700. In one implementation, the subject 700 is an eye of a human. The subject 700 may be prescribed to use the ophthalmic liquid medication 412 for treatment purposes.

As explained above, the subject 700 provides the input (i.e. the press input) on the dispensing button 116 for dropping the liquid medication 412 from the apparatus 100 on the ocular surface 702 of the subject 700. The subject 700 may be intended to use the liquid medication 412 of appropriate dosage (e.g., 40 uL) at prescribed time interval of the day. Thus, the subject 700 may provide appropriate press inputs on the dispensing button 116 for dispensing the liquid medication 412 over the ocular surface 702. In an example embodiment, the apparatus 100 may dispense an ear drops medication to an ear (not shown in Figures) of the subject 700.

In one scenario, the subject 700 may be intended to tilt the head backwards, hovering the nozzle 304 over the eye (or the ocular surface 702), for allowing the liquid medication 412 to fall on the ocular surface 702 dispensed through the nozzle 304 via gravity. In another scenario, the subject 700 may hold the apparatus 100 in an upright position such that the nozzle 304 is in close proximity to the top of a lower eyelid (not shown in Figures) of the subject 700. Thus, due to the close proximity, the intermolecular forces between the liquid medication 412 and the eye's moisture of the subject 700 may enable the liquid medication 412 to drop on the ocular surface 702, upon extrusion from the nozzle 304. Additionally, the predefined time (e.g., 2 seconds) allows the liquid medication 412 dropped over the ocular surface 702 to spread out over the ocular surface 702, thus mitigating the liquid medication 412 concentrating in one area on the eye and spilling over the eyelid.

Figure 8:
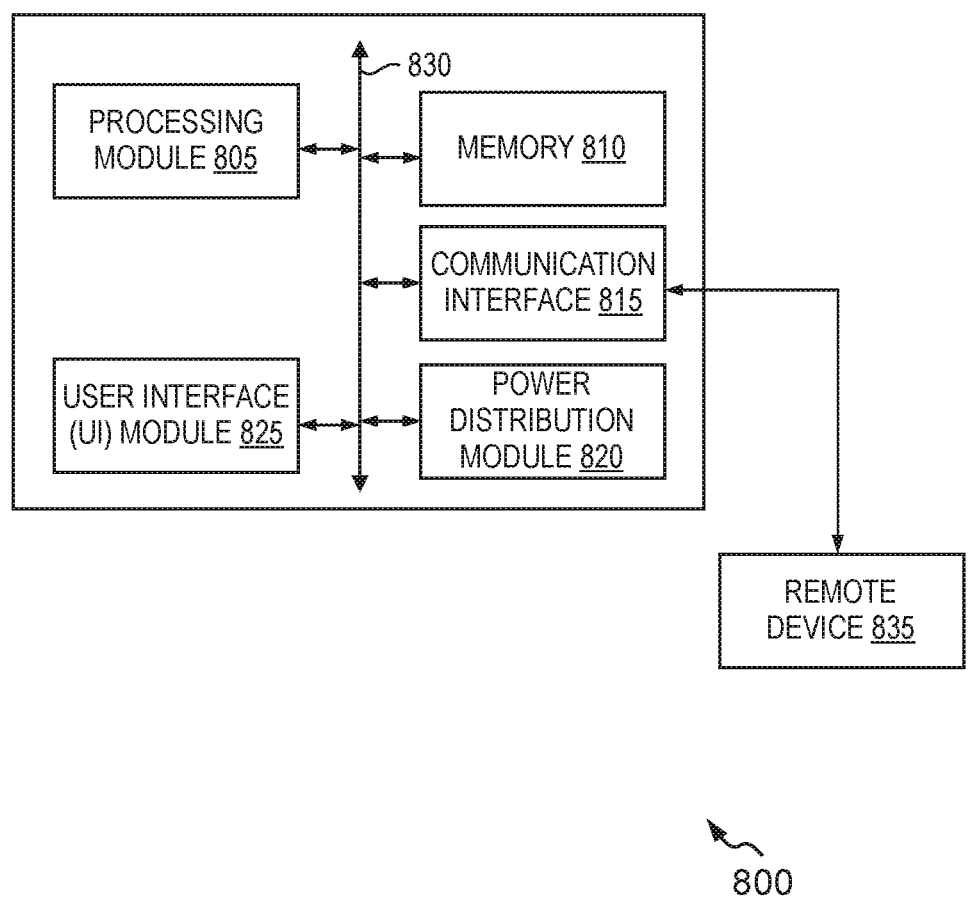
FIG. 8 illustrates a simplified block diagram representation of a control unit of the apparatus, in accordance with an example embodiment of the present disclosure.

FIG. 8 illustrates a simplified block diagram representation of a control unit 800 of the apparatus 100, in accordance with an example embodiment of the present disclosure. The control unit 800 is an example of the control unit 502 of FIG. 5. The control unit 800 includes at least one processing module 805, a memory 810, a communication interface 815, a power distribution module 820 and a user interface (UI) module 825. The one or more components of the control unit 800 communicate with each other via a centralized circuit system 830.

It is noted that although the control unit 800 is depicted to include only one processing module, the control unit 800 may include more number of processors therein. In an embodiment, the memory 810 is capable of storing executable instructions. Further, the processing module 805 is capable of executing the platform instructions to perform the operations described herein. In an embodiment, the processing module 805 may be embodied as a multi-core processor, a single core processor, or a combination of one or more multi-core processors and one or more single core processors.

The memory 810 may be embodied as one or more volatile memory devices, one or more non-volatile memory devices, and/or a combination of one or more volatile memory devices and non-volatile memory devices. Examples of the memory 810 include a random-access memory (RAM), a read-only memory (ROM), a removable storage drive, and the like. In at least some embodiments, the memory 810 stores instructions for enabling the processing module 805 to monitor signals from various circuitry of the apparatus 100, operate the apparatus 100 for dispensing the liquid medication, compute the one or more parameters, and the like. In some embodiments, the memory 810 may store the information related to the initial volume of the liquid medication.

The power distribution module 820 includes suitable logic and circuitry for managing the power supply to the control unit 800 and other components of the apparatus 100 for operating the apparatus 100. More specifically, the power distribution module 820 is communicably coupled to the battery 602 of the apparatus 100. The power distribution module 820 is configured to supply power to each of the components of the apparatus 100 upon powering on the apparatus 100, for dispensing the liquid medication 412.

The user interface (UI) module 825 includes suitable logic and circuitry configured to receive the input information from the subject 700 and transmit the input information to the processing module 805 for performing one or more operations described herein. The user interface module 825 is configured to receive the input information related to the initial volume of the liquid medication. Further, the user interface module 825 may provide the output (i.e. the one or more parameters) either in form of the visual information or the audio output to the subject 700. Examples of the user interface (UI) module 825 may include, but are not limited to, a touch screen, soft keys, a microphone, a speaker, a display such as a light emitting diode (LED) display, a thin-film transistor (TFT) display, a liquid crystal display, an active-matrix organic light-emitting diode (AMOLED) display, and the like.

The processing module 805 is configured to operate the apparatus 100 to dispense the liquid medication 412 in a controlled manner. The processing module 805 is configured to check the signals (i.e. the first signal and the second signal), upon pressing the dispensing button 116. Based on determining the signals, the processing module 805 is configured to operate the drive mechanism 402, for extruding the liquid medication 412 through the nozzle 304. More specifically, the processing module 805 provides the command signal to the drive mechanism 402 for dispensing the liquid medication 412. Additionally, the processing module 805 is configured to compute the one or more parameters, upon each dispensing. In some embodiments, the processing module 805 may record the dosage time, dosage volume and transmit the aforementioned information to a remote device 835 via the communication interface 815. The remote device 835 may be a server, or a cloud computing system which are communicably coupled to the apparatus 100. Further, the one or more steps performed by the control unit 800 are already explained above, and therefore it is not reiterated herein, for the sake of brevity.

Various embodiments of the disclosure, as discussed above, may be practiced with steps and/or operations in a different order, and/or with hardware elements in configurations, which are different than those which are disclosed. Therefore, although the disclosure has been described based upon these exemplary embodiments, it is noted that certain modifications, variations, and alternative constructions may be apparent and well within the spirit and scope of the disclosure.

Although various exemplary embodiments of the disclosure are described herein in a language specific to structural features and/or methodological acts, the subject matter defined in the appended claims is not necessarily limited to the specific features or acts described above. Rather, the specific features and acts described above are disclosed as exemplary forms of implementing the claims.

What is claimed is:

1. A liquid medication dispensing apparatus, the apparatus comprising:
a housing comprising an inner cavity and a cap hingedly coupled to an upper portion of the housing and operable between an open position and a closed position;
a cartridge assembly configured to be inserted in the inner cavity, the cartridge assembly comprising:
a support structure configured at a bottom portion of the cartridge assembly,
a mounting platform disposed on the support structure,
a nozzle base configured at a top portion of the cartridge assembly, the nozzle base comprising a nozzle, and
an intermediate body portion coupling the support structure and the nozzle base while maintaining a gap therebetween for securing a medication bottle between the nozzle base and the mounting platform; and
a control unit disposed in the housing, the control unit configured to at least:
receive a first signal from a circuitry associated with a dispensing button mounted to the housing, upon detection of an input on the dispensing button, and
upon receipt of the first signal, provide a command signal to a drive mechanism of the cartridge assembly, for retrieving a liquid medication from the medication bottle and extrude the liquid medication through the nozzle,
wherein the drive mechanism comprises: a piston chamber comprising an inlet fluidically coupled to an opening of the medication bottle and an outlet fluidically coupled to the nozzle via a tube; a plunger disposed within the piston chamber; and an actuator comprising a drive screw coupled to the plunger.

2. The apparatus as claimed in claim 1, wherein, upon receipt of the command signal, the actuator operates the drive screw to drive the plunger between a first position and a second position within the piston chamber for receiving the liquid medication within the piston chamber via the inlet, and to extrude the liquid medication through the nozzle via the tube fluidically coupled to the outlet, respectively.

3. The apparatus as claimed in claim 2, wherein the actuator operates to provide a rotational movement which is translated into a linear movement through the drive screw, for driving the plunger between the first position and the second position within the piston chamber.

4. The apparatus as claimed in claim 3, wherein the plunger operated between the first position and the second position creates a differential pressure within the piston chamber, which enables extruding of a metered volume of the liquid medication from the nozzle, for a predefined time.

5. The apparatus as claimed in claim 4, wherein the liquid medication is an ophthalmic liquid medication, for administering to an ocular surface of a subject.

6. The apparatus as claimed in claim 1, wherein the nozzle base is pivotally mounted to the intermediated body portion via a fastening member coupled to the nozzle base, the nozzle base operable between an unlocked state and a locked state, wherein,
in the unlocked state, the nozzle base is disengaged from the intermediate body portion, for allowing the medication bottle to be inserted in a groove of the mounting platform, and
in the locked state, the nozzle base is engaged to the intermediate body portion, such that the nozzle base, and the medication bottle are positioned along an axis of the cartridge assembly.

7. The apparatus as claimed in claim 1, further comprising: a latch mechanism coupled to the housing and the cap, the latch mechanism configured to temporarily engage the cap to the upper portion of the housing, when the cap is operated to the closed position.

8. The apparatus as claimed in claim 7, wherein the control unit is configured to determine, if the cap is operated in the open position, prior to providing the command signal to the drive mechanism for dispensing the liquid medication, wherein the control unit determines, if the cap operated in the open position, due to absence of a second signal from the latch mechanism.

9. The apparatus as claimed in claim 1, further comprising:
a cartridge gasket disposed in the cartridge assembly, for enabling an airtight seal between the medication bottle and the mounting platform, upon securing the medication bottle between the nozzle base and the mounting platform.

10. A liquid medication dispensing apparatus, the apparatus comprising:
a housing comprising an inner cavity and a cap hingedly coupled to an upper portion of the housing and operable between an open position and a closed position;
a dispensing button mounted to the upper portion of the housing;
a cartridge assembly configured to be inserted in the inner cavity, the cartridge assembly comprising:
a support structure configured at a bottom portion of the cartridge assembly,
a mounting platform disposed on the support structure,
a nozzle base configured at a top portion of the cartridge assembly, the nozzle base comprising a nozzle, and
an intermediate body portion coupling the support structure and the nozzle base while maintaining a gap therebetween for securing a medication bottle between the nozzle base and the mounting platform; and
a control unit disposed in the housing, the control unit configured to at least:
receive a first signal from a circuitry associated with the dispensing button, upon detection of an input on the dispensing button,
determine, if the cap is operated in the open position, based on a second signal from a latch mechanism coupled to the housing and the cap, and
based on determining the cap is operated in the open position, provide a command signal to a drive mechanism of the cartridge assembly, for retrieving a liquid medication from the medication bottle and extrude the liquid medication through the nozzle, for administering to an ocular surface of a subject.

11. The apparatus as claimed in claim 10, wherein the drive mechanism comprises:

a piston chamber comprising an inlet fluidically coupled to an opening of the medication bottle and an outlet fluidically coupled to the nozzle via a tube;
a plunger disposed within the piston chamber; and
an actuator comprising a drive screw coupled to the plunger.

12. The apparatus as claimed in claim 11, wherein, upon receipt of the command signal, the actuator operates the drive screw to drive the plunger between a first position and a second position within the piston chamber for receiving the liquid medication within the piston chamber via the inlet, and to extrude the liquid medication through the nozzle via the tube fluidically coupled to the outlet, respectively.

13. The apparatus as claimed in claim 12, wherein the actuator operates to provide a rotational movement which is translated into a linear movement through the drive screw, for driving the plunger between the first position and the second position within the piston chamber.

14. The apparatus as claimed in claim 13, wherein the plunger operated between the first position and the second position creates a differential pressure within the piston chamber, which enables extruding of a metered volume of the liquid medication from the nozzle, for a predefined time.

15. The apparatus as claimed in claim 10, wherein the liquid medication is an ophthalmic liquid medication, for administering to the ocular surface of the subject.

16. The apparatus as claimed in claim 10, wherein the nozzle base is pivotally mounted to the intermediated body portion via a fastening member coupled to the nozzle base, the nozzle base operable between an unlocked state and a locked state, wherein,
in the unlocked state, the nozzle base is disengaged from the intermediate body portion, for allowing the medication bottle to be inserted in a groove of the mounting platform, and
in the locked state, the nozzle base is engaged to the intermediate body portion, such that the nozzle base, and the medication bottle are positioned along an axis of the cartridge assembly.

17. The apparatus as claimed in claim 10, wherein the latch mechanism is coupled to the housing and the cap, the latch mechanism configured to temporarily engage the cap at the upper portion of the housing, when the cap is operated to the closed position.

18. An ophthalmic liquid medication dispensing apparatus, the apparatus comprising:
a housing comprising an inner cavity and a cap hingedly coupled to an upper portion of the housing and operable between an open position and a closed position;
a dispensing button mounted to the upper portion of the housing;
a cartridge assembly configured to be inserted in the inner cavity, the cartridge assembly comprising:
a support structure configured at a bottom portion of the cartridge assembly,
a mounting platform disposed on the support structure,
a nozzle base configured at a top portion of the cartridge assembly, the nozzle base comprising a nozzle,
an intermediate body portion coupling the support structure and the nozzle base while maintaining a gap therebetween for securing a medication bottle between the nozzle base and the mounting platform, and
a drive mechanism, comprising:
a piston chamber comprising an inlet fluidically coupled to an opening of the medication bottle and an outlet fluidically coupled to the nozzle via a tube,
a plunger disposed within the piston chamber, and
an actuator comprising a drive screw coupled to the plunger; and
a control unit disposed in the housing, the control unit configured to at least:
receive a first signal from a circuitry associated with the dispensing button, upon detection of an input on the dispensing button,
determine, if the cap is operated in the open position, based on a second signal from a latch mechanism coupled to the housing and the cap, and
based on determining the cap is operated in the open position, provide a command signal to the drive mechanism, for retrieving a liquid medication from the medication bottle and extrude the liquid medication through the nozzle,
wherein, upon receipt of the command signal, the actuator operates the drive screw to drive the plunger between a first position and a second position within the piston chamber for receiving the liquid medication within the piston chamber via the inlet, and to extrude the liquid medication through the nozzle via the tube fluidically coupled to the outlet, respectively, and
wherein the plunger operated between the first position and the second position creates a differential pressure within the piston chamber, which enables extruding of a metered volume of the liquid medication through the nozzle, for a predefined time, wherein the liquid medication is an ophthalmic liquid medication, for administering to an ocular surface of a subject.

19. The apparatus as claimed in claim 18, wherein the nozzle base is pivotally mounted to the intermediated body portion via a fastening member coupled to the nozzle base, the nozzle base operable between an unlocked state and a locked state, wherein, in the unlocked state, the nozzle base is disengaged from the intermediate body portion, for allowing the medication bottle to be inserted in a groove of the mounting platform, and in the locked state, the nozzle base is engaged to the intermediate body portion, such that the nozzle base, and the medication bottle are positioned along an axis of the cartridge assembly.

* * * * *